(12) United States Patent
Van Broekhoven et al.

(10) Patent No.: US 7,176,340 B2
(45) Date of Patent: *Feb. 13, 2007

(54) CONTINUOUS PROCESS FOR THE ALKYLATION OF HYDROCARBONS

(75) Inventors: Emanuel Hermanus Van Broekhoven, Monnickendam (NL); Johannes Wilhelmus Maria Sonnemans, Soest (NL); Stephan Zuijdendorp, Zaandam (NL)

(73) Assignee: Albemarle Netherlands B.V., Amersfoort (NL)

( * ) Notice: Subject to any disclaimer, the term of this patent is extended or adjusted under 35 U.S.C. 154(b) by 655 days.

This patent is subject to a terminal disclaimer.

(21) Appl. No.: 10/163,108

(22) Filed: Jun. 5, 2002

(65) Prior Publication Data

US 2002/0198421 A1   Dec. 26, 2002

(30) Foreign Application Priority Data

Aug. 6, 2001   (EP) .................................. 01202206

(51) Int. Cl.
*C07C 2/64* (2006.01)
*C07C 2/54* (2006.01)

(52) U.S. Cl. ...................... 585/449; 585/301; 585/312; 585/709; 585/714; 585/716; 585/719

(58) Field of Classification Search ............... 585/301, 585/312, 709, 714, 716, 719, 449
See application file for complete search history.

(56) References Cited

U.S. PATENT DOCUMENTS

| 2,406,709 | A | 8/1946 | Pevere ..................... 260/683.4 |
| 3,236,912 | A | 2/1966 | Phillips .................. 260/683.45 |
| 4,008,291 | A | 2/1977 | Zabransky et al. .... 260/683.43 |
| 5,523,503 | A | 6/1996 | Funk et al. ................. 585/446 |

FOREIGN PATENT DOCUMENTS

| EP | 1 070 694 | 1/2001 |
| WO | WO 98/23560 | 6/1998 |

OTHER PUBLICATIONS

International Search Report of Application No. PCT/EP 02/05760 dated Jul. 18, 2002.

*Primary Examiner*—Thuan Dinh Dang
(74) *Attorney, Agent, or Firm*—Frank C. Eymard

(57) ABSTRACT

A continuous alkylation process performed in an apparatus comprising a series of at least two zone A reactors and a series of at least two zone B reactors, in which the zone A reactors and the zone B reactors cycle between alkylation mode and mild regeneration mode, and wherein the alkylation mode comprises introducing an alkylation agent into a first reactor of the zone through which the alkylatable compound passes, reacting a portion of the alkylatable compound with a portion of the alkylation agent to produce a product stream, and performing this operation at least once more in a downstream reactor in the same zone employing, instead of alkylatable compound, a stream comprising the product stream.

37 Claims, 1 Drawing Sheet

CONTINUOUS PROCESS FOR THE ALKYLATION OF HYDROCARBONS

CROSS REFERENCE TO RELATED APPLICATION

This application claims priority from European Patent Application No. EP 01202206.7, filed Jun. 8, 2001.

BACKGROUND OF THE INVENTION

1. Field of the Invention

This invention relates to a continuous process for the alkylation of hydrocarbons over a solid acid catalyst, and more in particular a process in which the catalyst is also regenerated.

2. Prior Art

Within the framework of the present invention, the term alkylation refers to the reaction of an alkylatable compound, such as an aromatic or a saturated hydrocarbon, with an alkylation agent, such as an olefin. Without limiting its scope, we will further illustrate the invention by discussing the alkylation of saturated hydrocarbons, in general branched saturated hydrocarbons, with an olefin to give highly branched saturated hydrocarbons with a higher molecular weight.

U.S. Pat. No. 5,523,503 discloses the alkylation of hydrocarbons, i.e. isobutane, in an apparatus comprising at least three reactors. The reactors cycle between a zone in which alkylation is performed and a zone where the catalyst is regenerated. Cycling of the reactors between the two zones occurs by periodically advancing the locations at which the first feed stream and the regenerant stream enter the process in a manner such as to simulate the cocurrent movement of the beds of catalysts relative to the direction of the liquid phase reactant flow.

In this process, the points of feed and regenerant injection move along the reactors. Such a process requires a lot of valves and tubing. A second disadvantage of this process is the need for the introduction into the apparatus of two separate isobutane-containing streams: a feed stream and a regenerant stream. A third disadvantage is that before cycling a reactor from the regeneration to the alkylation zone and vice versa, the reactor needs to be flushed.

SUMMARY OF THE INVENTION

In a primary embodiment, the present invention comprises a continuous alkylation process wherein an alkylatable compound is reacted with an alkylation agent in the presence of a solid acid alkylation catalyst to form an alkylate and wherein the catalyst is regenerated, said process being performed in an apparatus comprising a series of at least two catalyst-containing reactors in a zone A and a series of at least two catalyst-containing reactors in a zone B, in which process (a) zone A reactors and zone B reactors cycle back and forth per zone between alkylation mode and mild regeneration mode,
(b) the alkylation mode comprises introducing an alkylation agent into a first reactor of the zone through which the alkylatable compound passes, reacting a portion of the alkylatable compound with at least a portion of the alkylation agent to produce an alkylate-containing product stream, and performing this operation at least once more in a downstream reactor in the same zone employing, instead of said alkylatable compound, a stream comprising said alkylate-containing product stream which may or may not have been subjected to a prior intermittent separation during which a portion of the alkylate has been removed, to produce an alkylation mode alkylate-containing effluent,
(c) the mild regeneration mode comprises contacting the solid acid alkylation catalyst with hydrogen in each of the at least two reactors of the zone,
(d) alkylate is recovered.

Other embodiments of the invention relate to variations in process configurations, reactants and reaction conditions, each of which is discussed in detail hereinbelow.

BRIEF DESCRIPTION OF THE DRAWING

The process configuration of the invention is shown in FIG. 1

DETAILED DESCRIPTION OF THE INVENTION

Figure 1:
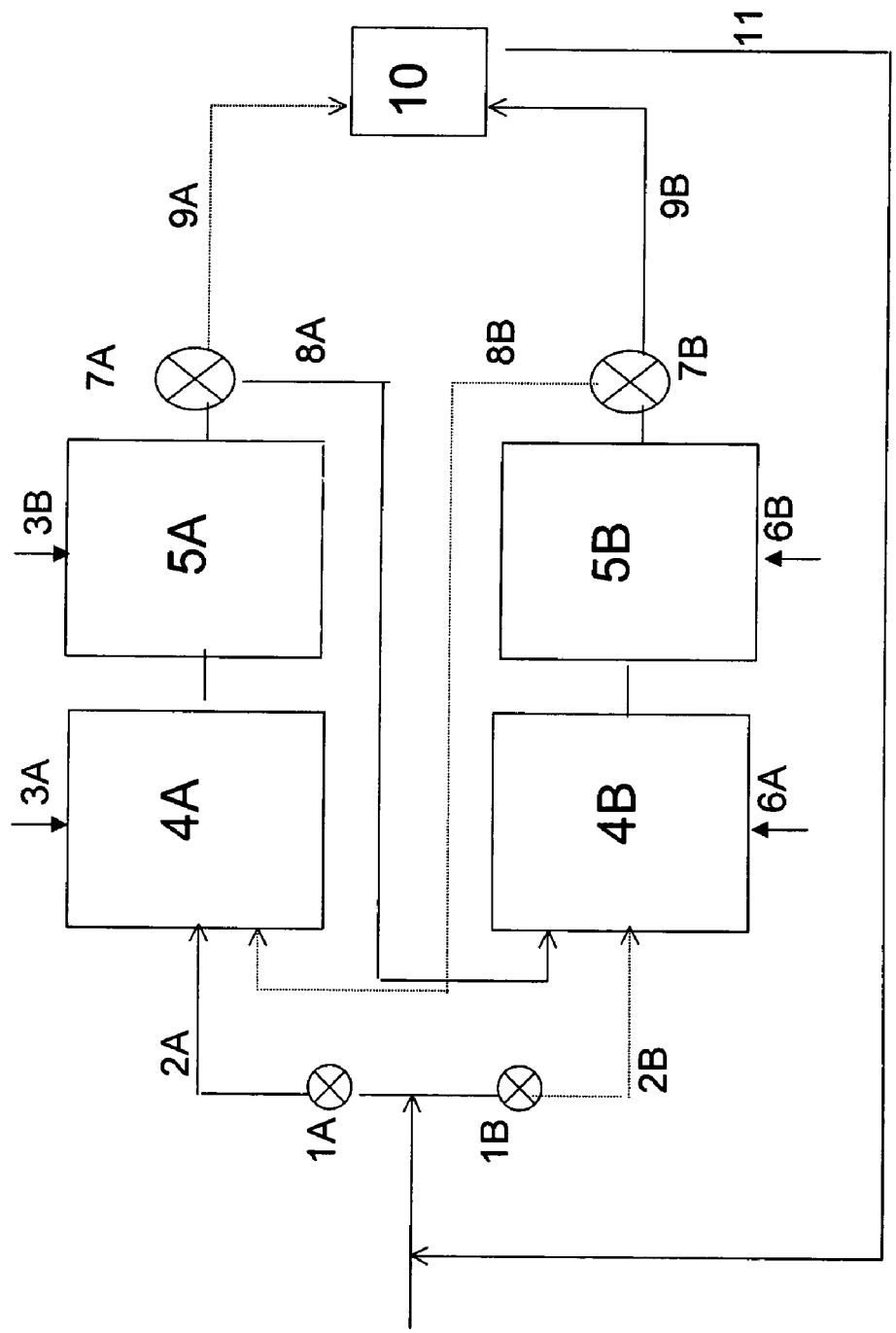

The advantage of the process of the invention is that the reactors in zone A and zone B can cycle between the alkylation and the regeneration mode just by switching a few valves, instead of the injection points having to be moved. Moreover, instead of two separate alkylatable compound-containing streams, i.e. a feed stream and a regenerant stream, only one hydrocarbon-containing stream is required: the alkylatable compound-containing stream. Regeneration is performed in a stream comprising hydrocarbon or in isolated reactors. If a stream is employed, the hydrocarbon will comprise alkylatable compound, or at least a portion of the alkylation mode alkylate-containing effluent. If regeneration is performed in isolated reactors, alkylate will be present in the reactors. This alkylate results from when the reactors in this zone operated in the alkylation mode.

We have discovered that alkylate remains essentially unconverted when present during regeneration of the catalyst with hydrogen. Therefore, in this process there is no need to remove the alkylate from the reactor system before cycling from the regeneration to the alkylation mode.

It is to be understood that during operation in the regeneration mode there may be time periods when the catalyst is not contacted with hydrogen. Analogously, during operation in the alkylation mode there may be time periods when no alkylation agent is introduced.

FIG. 1 shows a schematic lay-out of an apparatus suitable for carrying out the process according to the invention. By way of example, this FIGURE displays only four solid acid alkylation catalyst-containing reactors: two in zone A and two in zone B. Note that according to the invention, the apparatus contains at least two reactors in zone A and at least two reactors in zone B. Preferred configurations are two reactors in zone A and two reactors in zone B or three reactors in zone A and three reactors in zone B.

The reactors contain the solid acid alkylation catalyst and are equipped with standard equipment known in the art for measuring temperature, pressure, and flow. The catalyst can be present in any type of catalyst bed, for instance a fluidised bed, a fixed bed or suspended in a slurry. Moreover, the reactors can contain more than one catalyst bed. This allows for the use in one reactor of catalyst beds with different catalyst compositions and/or of different size. For instance, the most downstream catalyst bed can be larger, i.e. contain a larger amount of catalyst, and/or can contain a more active catalyst than the upstream catalyst beds in the same reactor.

This can be useful for reaching complete conversion of the alkylation agent, thereby preventing breakthrough of this compound.

When using at least two catalyst beds in a reactor, it is preferred that each of these catalyst beds is provided with its own addition of alkylation agent, so that the total amount of olefin needed in the reactor is spread over several injection points. This results in higher molar ratios of alkylatable compound to alkylation agent in the reactor. The injection points are located below each of the catalyst beds, i.e. below the most upstream bed and below each of the subsequent catalyst beds. Before entering the catalyst bed, the injected alkylation agent is preferably mixed with the alkylatable compound already present in the reactor.

Alternatively, it is possible to use at least two catalyst beds in a reactor and inject alkylation agent below each of the catalyst beds except for the most downstream one. This can also stimulate complete conversion of the alkylation agent in the reactor and prevent breakthrough of this compound. Furthermore, it is possible to use at least two catalyst beds in a reactor and inject different alkylation agents below the different catalyst beds. For instance, butene can be added to the first two beds, whereas propene is added to the third catalyst bed.

The apparatus of FIG. 1 comprises reactors 4A and 5A in zone A, which zone is in the alkylation mode. To reactor 4A, alkylatable compound is fed via valve system 1A and duct 2A, and the alkylation agent is fed through inlet 3A. The two components can (partially) react to produce an alkylate-containing product stream. This product stream is subsequently led to reactor 5A. Alkylation agent is fed to this reactor through inlet 3B. In this reactor the alkylation agent can (partially) react with alkylatable compound present in the alkylate-containing product stream to produce an alkylation mode alkylate-containing effluent.

Optionally, the alkylate or a portion of the alkylate may be removed from the alkylate-containing product stream before this stream enters reactor 5A, by means of an intermittent separation step. Preferably, such intermittent separation is performed between each of the reactors operating in the alkylation mode.

Losses of alkylatable compound during this separation step can be compensated for by subsequent addition of alkylatable compound to the alkylate-containing product stream.

This intermittent separation step offers a way to obtain an almost constant alkylate concentration throughout the whole apparatus. With such an almost constant alkylate concentration, the catalyst in the at least two reactors per zone will deactivate at almost equal rate.

Valve systems 1A, 1B, 7A, and 7B are only schematically represented in FIG. 1. Preferably, these valve systems are sets of valves and/or flow controllers which regulate the streams in ducts 2A, 2B, 8A and 9A, and 8B and 9B, respectively. The advantage of such sets of valves and/or flow controllers is that for instance the stream of alkylatable compound through duct 9A is not necessarily blocked the moment it is introduced into duct 8A, as will be the case when using, e.g., three-way valves. Moreover, flow controllers offer the possibility of regulating the streams flowing through the ducts.

In a first embodiment of the present invention, at least a portion of the alkylation mode alkylate-containing effluent is led via valve system 7A and through duct 8A to zone B, which contains reactors 4B and 5B, which reactors are in the regeneration mode. If only a portion of the alkylation mode alkylate-containing effluent is led to zone B, the remaining portion of the alkylation mode alkylate-containing effluent can be led through duct 9A to separation unit 10. If desired, alkylatable compound may be added to the portion of the alkylation mode alkylate-containing effluent which is led to zone B. In this embodiment it is preferred, however, to lead the entire alkylation mode alkylate-containing effluent to zone B.

Hydrogen is fed to reactor 4B or to both reactor 4B and reactor 5B through inlet 6A and inlets 6A and 6B, respectively. The alkylation mode alkylate-containing effluent which is led to zone B is first introduced into reactor 4B. Subsequently, the effluent of reactor 4B, which is a mixture comprising the alkylation mode alkylate-containing effluent and hydrogen, is introduced into reactor 5B to produce a regeneration mode effluent. This regeneration mode effluent is then led via valve system 7B and through duct 9B to separation unit 10.

The separation unit may comprise one or more devices. In this separation unit alkylatable compound is separated from the effluents fed to this separation unit. At least a portion of this alkylatable compound is recycled to zone A and/or zone B, i.e. the alkylation mode zone and/or the regeneration mode zone, as an alkylatable compound-containing stream. In this figure, by way of example, this alkylatable compound-containing stream is recycled through duct 11. Note that the stream and, therefore, the alkylatable compound introduced into reactor 4A, may contain other compounds such as alkylate. Other streams leaving the separation unit comprise the alkylate and usually also comprise a stream containing "lights", such as hydrogen and/or propane, and an n-alkanes-containing stream.

According to this first embodiment, the reactors in zone A and zone B can cycle between the alkylation mode and the regeneration mode by, e.g., (i) switching the streams coming through inlets 3A/B and 6A/B and (ii) changing the streams flowing through the different ducts. In this mode, hydrogen is fed to reactor 4A or to reactors 4A and 5A both, and the alkylation agent is fed to reactors 4B and 5B. Alkylatable compound is fed through duct 2B to reactor 4B and at least a portion of the alkylation mode alkylate-containing effluent is led via valve system 7B and through duct 8B to reactor 4A. If only a portion of the alkylation mode alkylate-containing effluent is led to reactor 4A, the remaining portion of the alkylation mode alkylate-containing effluent is led via duct 9B to separation unit 10. The regeneration mode effluent coming out of reactor 5A is led via valve system 7A and through duct 9A to separation unit 10.

In a second embodiment, the entire alkylation mode alkylate-containing effluent is led through duct 9A to separation unit 10. At the same time, alkylatable compound is introduced via duct 2B into reactor 4B, which is in the regeneration mode. The effluent of this reactor is subsequently led to reactor 5B. The effluent of reactor 5B, i.e. the regeneration mode effluent, is then led via valve system 7B and through duct 9B to separation unit 10. The reactors in zone A and zone B can be cycled between the alkylation mode and the regeneration mode by switching the streams coming through inlets 3A/B and 6A/B. By switching the streams coming through inlets 3A/B and 6A/B hydrogen is fed to reactor 4A or to reactors 4A and 5A both and the alkylation agent is fed to reactors 4B and 5B.

In a third embodiment, no streams are introduced into reactor 4B via ducts 2B or 8A while reactors 4B and 5B are operating in the regeneration mode, and the entire alkylation mode alkylate-containing effluent is led through duct 9A to separation unit 10. Alkylate, formed during the time when reactors 4B and 5B operated in the alkylation mode, is still present in these reactors. In principle, reactors 4B and 5B will be isolated from the system, meaning that no streams leave the reactor via valve system 7B during the regeneration period. However, it may be necessary to relieve the pressure from the reactor, e.g. via duct 9B.

The reactors in zone A and zone B can be cycled between the alkylation mode and the regeneration mode by, e.g., (i) switching the streams coming through inlets 3A/B and 6A/B and (ii) changing the streams through ducts 2A and 2B. In this mode, hydrogen is fed to reactor 4A or to reactors 4A and 5A both and the alkylation agent is fed to reactors 4B and 5B. In this embodiment it is preferred to feed hydrogen to reactors 4A and 5A both. Alkylatable compound is fed to reactor 4B, and no streams enter reactor 4A via duct 2A or duct 8B.

The process is typically performed under conditions such that at least a portion of the alkylation agent and the alkylatable compound are in the liquid phase or the supercritical phase. In general, the process according to the invention is performed at a temperature in the range of 233 to 523 K, preferably in the range of 293 to 423 K, more preferably in the range of 338 to 368 K, and a pressure in the range of 1 to 100 bar, preferably 5 to 40 bar, more preferably 15 to 30 bar.

In general, the mild regeneration step is carried out at a temperature in the range of 233 to 523 K and a pressure from 1 to 100 bar. Although the regeneration and alkylation steps can be performed at different temperatures and pressures, it is preferred for the regeneration temperature, expressed in K, and the regeneration pressure not to differ from the reaction temperature and the reaction pressure by more than 20%, more preferably not by more than 10%, still more preferably not by more than 5%. Most preferably, the regeneration temperature and pressure and the reaction temperature and pressure are essentially the same.

The molar ratio of alkylatable compound to alkylation agent in the total feed in the reactors preferably is higher than 5:1, more preferably higher than 50:1. Higher molar ratios are considered preferred for performance reasons, because they generally yield an increase in octane number and stability. The upper limit for this ratio is determined by the type of process applied, and by the process economics. It is not critical, and may be as high as 5,000:1. Generally, figures of, e.g., 1,000:1 or lower are preferred. These high molar ratios can be obtained in various ways known to the skilled person, e.g., by multiple inlets for alkylation agent or internal recycling of reactor contents. At this moment a molar ratio of alkylatable compound to alkylation agent of 150–750:1 is considered most preferred.

The feed rate (WHSV) of the alkylation agent generally is in the range of 0.01 to 5, preferably in the range of 0.05 to 0.5, more preferably in the range of 0.1 to 0.3 gram of alkylation agent per gram of catalyst per hour.

The catalyst is regenerated by being contacted with hydrogen in the presence of hydrocarbon, which comprises the alkylation mode alkylate-containing effluent, the alkylatable compound or the formed alkylate which is already present in the reactor. Typically, the hydrogen will be dissolved in the hydrocarbon. Preferably, the solution contains at least 10% of the saturation concentration of hydrogen, said saturation concentration being defined as the maximum quantity of hydrogen which can be dissolved in the hydrocarbon at regeneration temperature and pressure. Depending on the applied feed rates it may be more preferred for the solution to contain at least 50% of the saturation concentration, even more preferably at least 85%. At relatively low feed rates it is generally preferred to have as saturated a solution of hydrogen in the mixture as possible.

The frequency of cycling the zones between the alkylation mode and the regeneration mode, i.e. the regeneration frequency, depends on a number of conditions, including the nature of the catalyst, the reaction and regeneration conditions, and the amount of hydrogen present during the regeneration step. Preferably, the regeneration is performed before there is any substantial decrease of catalytic activity. Such a decrease can be observed by breakthrough of alkylation agent, which can be measured by analysing the concentration of alkylation agent in the alkylation mode alkylate-containing effluent. By cycling the zones between the alkylation and regeneration modes prior to breakthrough of alkylation agent it is possible to obtain a product of nearly constant composition in a high yield. Typically, the zones are switched between the alkylation and the regeneration mode with a frequency in the range of once per 10 hours to 10 times per hour, preferably once per 3 hours to 3 times per hour and even more preferably once per 2 hours to 2 times per hour.

Optionally, the reactors may be flushed with a stream containing hydrocarbon, e.g., an alkylatable compound-containing stream or an alkylation mode alkylate-containing effluent, before cycling of the zones from the alkylation to the regeneration mode or vice versa, in order to prevent hydrogen from being contacted with olefin, which would result in the formation of unwanted alkanes.

The apparatus may comprise one or more additional solid acid alkylation catalyst-containing reactors which can replace one or more of the at least two reactors in zone A and zone B. Preferably, the apparatus contains one such additional reactor. The availability of such additional reactors makes the process very flexible. If, owing to circumstances, the catalyst in one or more of the reactors deactivates to an unacceptable extent during the process, it can be replaced with one or more additional catalyst-containing reactors. The deactivated catalyst can then be regenerated by contacting it with hydrogen at high temperature in the gas phase to recover its original activity without affecting the ongoing alkylation process. After this high-temperature regeneration the reactor containing the high-temperature regenerated catalyst can serve as said additional reactor.

The high-temperature regeneration is effected at a temperature of at least 423 K, preferably in the range of 423–873, more preferably 473–673 K. To effect a long-term process on a commercial scale one can, e.g., carry out such a high-temperature regeneration after every 50, preferably after every 100 regenerations under mild conditions. Pilot plant experiments have shown that it is possible to effect a long-term process when the catalyst is subjected to a high-temperature regeneration after every 200–400 regenerations under mild conditions. Depending on the exact process variables on a commercial scale, this value may be higher or lower in actual practice.

The apparatus may also comprise an additional reactor at the downstream end of the zone operating in the alkylation mode into which no alkylation agent is introduced. This may help in obtaining a full conversion of the alkylation agent to alkylate. One such reactor can be used, which reactor cycles between zones A and B, or both zone A and zone B can comprise such an additional reactor. Alternatively, if a reactor contains more than one catalyst bed, the bed which is most downstream can be deprived of a separate olefin addition.

Preferred alkylatable compounds to be used in the process according to the invention are isoalkanes having 4–10 carbon atoms, such as isobutane, isopentane, isohexane or mixtures thereof.

Preferred alkylation agents are olefins having 2–10 carbon atoms, preferably 2–6 carbon atoms, more preferably 3–5 carbon atoms, e.g., propene, butene, pentene. The alkylation of isobutane with butene or a mixture of butenes constitutes an attractive embodiment of the process according to the invention.

The solid acid alkylation catalyst used in the process according to the invention comprises a hydrogenating metal component and a solid acid constituent.

Examples of suitable hydrogenating metal components are constituents of the transition metals, such as metals of Group VIII of the Periodic Table, or mixtures thereof. Among these, noble metals of Group VIII of the Periodic Table are preferred. Platinum, palladium, and mixtures thereof are especially preferred. The amount of hydrogenating metal component will be dependent on its nature. When the hydrogenating metal component is a noble metal of Group VIII of the Periodic Table, the catalyst generally will contain in the range of 0.01 to 2 wt. % of the metal, preferably 0.1–1 wt. %, calculated as metal.

Examples of solid acid constituents are zeolites such as zeolite beta, MCM-22, MCM-36, mordenite, X-zeolites and Y-zeolites, including H-Y-zeolites and USY-zeolites, non-zeolitic solid acids such as silica-alumina, sulphated oxides such as sulphated oxides of zirconium, titanium, or tin, sulphated mixed oxides of zirconium, molybdenum, tungsten, etc., and chlorinated aluminium oxides. The presently preferred solid acid constituents are zeolites, including mordenite, zeolite beta, X-zeolites and Y-zeolites, including H-Y-zeolites and USY-zeolites, sulphated oxides, and chlorinated aluminium oxides. Mixtures of solid acid constituents can also be employed.

The catalyst to be used in the process according to the invention preferably comprises a hydrogenating metal component on a carrier which comprises 2–98 wt. % of solid acid constituent and 98–2 wt. % of a matrix material, calculated on the carrier. Preferably, the carrier comprises 10–90 wt. % of matrix material, and 90–10 wt. % of solid acid constituent. More preferably, the carrier comprises 10–80 wt. % of matrix material and the balance is solid acid constituent. Especially preferred is the catalyst wherein the carrier comprises 10–40 wt. % of matrix material and the balance is solid acid constituent.

In the present specification the term matrix material encompasses all components which are present in the catalyst except for the solid acid constituent and the hydrogenating metal component. Examples of suitable matrix materials are alumina, silica, clays, and mixtures thereof. Matrix materials comprising alumina are generally preferred. A matrix material which consists essentially of alumina is considered most preferred at this point in time.

Preferably, the catalyst to be used in the process according to the invention has a particle size of at least 0.5 mm. Preferably, the particle size is at least 0.8 mm, more preferably at least 1.0 mm. The upper limit of the particle size preferably lies at 10 mm, more preferably at 5 mm, even more preferably at 3 mm.

In the present specification, the term particle size is defined as the average diameter of the solid part of the catalyst, as will be clear to the skilled person.

The catalyst can be prepared by processes common to the industry. These will comprise, say, shaping the solid acid constituent after mixing it with a matrix material, to form particles, followed by calcination of the particles. The hydrogenating function may, e.g., be incorporated into the catalyst composition by impregnating the carrier particles with a solution of a hydrogenation metal component.

Preferred alkylates to be produced by the process according to the invention are $C_5+$ alkylates with a minimum of $C_9+$ alkylates. The $C_5+$ alkylate obtained using the process according to the invention preferably has a $C_9+$ content of less than 30 wt. %, more preferably of less than 20 wt. %, most preferably of less than 10 wt. %. Frequent catalyst regeneration enables $C_9+$ production to be controlled at a comparatively low level.

Also, depending on the regeneration frequency, in the process according to the invention a high $C_5+$ alkylate yield is obtained. The process according to the invention makes it possible to obtain a $C_5+$ alkylate yield in excess of 200%, calculated on the weight of the consumed olefin, preferably of 204% or higher. The quality of the alkylate product obtained in the process according to the invention can be measured by the RON of the product. The RON is a measure of the anti-knock rating of gasoline and/or gasoline constituents. The higher the RON, the more favourable the anti-knock rating of the gasoline will be. Depending on the type of gasoline engine, generally speaking a higher anti-knock rating is of advantage when it comes to the working of the engine. The product obtained in the process according to the invention preferably has a RON of 90 or higher, more preferably of 92 or higher, most preferably 94 or higher. The RON is obtained by determining, e.g., via gas chromatography, the percentage by volume of the various hydrocarbons in the product. The percentages by volume are then multiplied by the RON contribution and added up.

Examples of compounds with a RON of 90 or higher are isopentane, 2,2-dimethyl butane, 2,3-dimethyl butane, trimethyl butane, 2,3-dimethyl pentane, 2,2,4-trimethyl pentane, 2,2,3-trimethyl pentane, 2,3,4-trimethyl pentane, 2,3,3-trimethyl pentane, and 2,2,5-trimethyl hexane.

The invention claimed is:

1. A continuous alkylation process wherein an alkylatable compound is reacted with an alkylation agent in the presence of a solid acid alkylation catalyst to form an alkylate and wherein the catalyst is regenerated, said process being performed in a series of at least two catalyst-containing reactors in a zone A and a series of at least two catalyst-containing reactors in a zone B, in which process
    (a) the zone A reactors and the zone B reactors cycle back and forth per zone between alkylation mode and mild regeneration mode,
    (b) the alkylation mode comprises introducing an alkylation agent into a first reactor of the zone that is in the alkylation mode, reacting a portion of the alkylatable compound with at least a portion of the alkylation agent to produce an alkylate-containing product stream, and performing this operation at least once more in a downstream reactor in the zone that is in the alkylation mode employing, instead of said alkylatable compound, a stream comprising said alkylate-containing product stream, to produce an alkylation mode alkylate-containing effluent,
    (c) the mild regeneration mode comprises contacting the solid acid alkylation catalyst with hydrogen in each of the at least two reactors of the zone that is in the mild regeneration mode,
    (d) alkylate is recovered.

2. The process of claim 1 wherein before performing said operation in step (b) in said downstream reactor, said stream comprising said alkylate-containing product stream has been subjected to a prior intermittent separation during which a portion of the alkylate has been removed.

3. The process of claim 1 wherein the mild regeneration mode comprises contacting the solid acid alkylation catalyst with a portion of the alkylation mode alkylate-containing effluent and hydrogen in the first reactor of the zone that is in the mild regeneration mode, and performing this operation at least once more in a downstream reactor in the zone that is in the mild regeneration mode employing, instead of said portion of the alkylation mode alkylate-containing effluent, the effluent of the preceding upstream reactor, to produce a regeneration mode effluent, and wherein alkylate is recovered from the regeneration mode effluent and from the remaining portion of the alkylation mode alkylate-containing effluent.

4. The process of claim 1 wherein the mild regeneration mode comprises contacting the solid acid alkylation catalyst with the entire alkylation mode alkylate-containing effluent and hydrogen in the first reactor of the zone that is in the mild regeneration mode, and performing this operation at least once more in a downstream reactor in the zone that is in the mild regeneration mode employing, instead of said alkylation mode alkylate-containing effluent, the effluent of the preceding upstreamreactor, to produce a regeneration mode effluent, and wherein alkylate is recovered from said regeneration mode effluent.

5. The process of claim 1 wherein the mild regeneration mode comprises contacting the solid acid alkylation catalyst with the alkylatable compound and hydrogen in the first reactor of the zone that is in the mild regeneration mode, and performing this operation at least once more in a downstream reactor in the same zone that is in the mild regeneration mode employing, instead of said alkylatable compound, the effluent of the preceding upstream reactor, to produce a regeneration mode effluent, and wherein alkylate is recovered from the alkylation mode alkylate-containing effluent and the regeneration mode effluent.

6. The process of claim 1 wherein the mild regeneration mode comprises contacting the solid acid alkylation catalyst with hydrogen in each of the at least two reactors, which reactors contain alkylate formed in said at least two reactors during their previous cycle of operation in the alkylation mode, and wherein alkylate is recovered from the alkylation mode alkylate-containing effluent.

7. The process of claim 3 wherein a separation unit separates alkylatable compound from the alkylation mode alkylate-containing effluent and from the regeneration mode effluent, after which a stream comprising at least a portion of the alkylatable compound is recycled to the zone operating in the alkylation mode.

8. The process of claim 5 wherein a separation unit separates alkylatable compound from the alkylation mode alkylate-containing effluent and from the regeneration mode effluent, after which a stream comprising at least a portion of the alkylatable compound is recycled to the zone operating in the alkylation mode.

9. The process of claim 4 wherein a separation unit separates alkylatable compound from the regeneration mode effluent, after which a stream comprising at least a portion of the alkylatable compound is recycled to the zone operating in the alkylation mode.

10. The process of claim 6 wherein a separation unit separates alkylatable compound from the alkylation mode alkylate-containing effluent, after which a stream comprising at least a portion of the alkylatable compound is recycled to the zone operating in the alkylation mode.

11. The process of claim 3 wherein a separation unit separates alkylatable compound from the alkylation mode alkylate-containing effluent and from the regeneration mode effluent, after which a stream comprising at least a portion of the alkylatable compound is recycled to the zone operating in the regeneration mode.

12. The process of claim 5 wherein a separation unit separates alkylatable compound from the alkylation mode alkylate-containing effluent and from the regeneration mode effluent, after which a stream comprising at least a portion of the alkylatable compound is recycled to the zone operating in the regeneration mode.

13. The process of claim 7 wherein a separation unit separates alkylatable compound from the alkylation mode alkylate-containing effluent and from the regeneration mode effluent, after which a stream comprising at least a portion of the alkylatable compound is recycled to the zone operating in the regeneration mode.

14. The process of claim 4 wherein a separation unit separates alkylatable compound from the regeneration mode effluent, after which a stream comprising at least a portion of the alkylatable compound is recycled to the zone operating in the regeneration mode.

15. The process of claim 9 wherein a separation unit separates alkylatable compound from the regeneration mode effluent, after which a stream comprising at least a portion of the alkylatable compound is recycled to the zone operating in the regeneration mode.

16. The process of claim 6 wherein a separation unit separates alkylatable compound from the alkylation mode alkylate-containing effluent, after which a stream comprising at least a portion of the alkylatable compound is recycled to the zone operating in the regeneration mode.

17. The process of claim 10 wherein a separation unit separates alkylatable compound from the alkylation mode alkylate-containing effluent, after which a stream comprising at least a portion of the alkylatable compound is recycled to the zone operating in the regeneration mode.

18. The process of claim 1 wherein each of zone A and zone B comprises two reactors.

19. The process of claim 18 wherein a separation unit is between the two reactors in the zone operating in the alkylation mode, by which a portion of the alkylate can be removed from the alkylate-containing product stream.

20. The process of claim 1 wherein the apparatus comprises three reactors in zone A and three reactors in zone B.

21. The process of claim 20 wherein a separation unit is between the first and the second as well as between the second and the third reactor in the zone operating in the alkylation mode, by which a portion of the alkylate can be removed from the alkylate.-containing product stream.

22. The process according of claim 1 wherein the at least two reactors in zone A and the at least two reactors in zone B each comprise more than one catalyst bed with separate addition of alkylation agent.

23. The process of claim 22 wherein the catalyst bed at the most downstream end of the zone operating in the alkylation mode is deprived of separate addition of alkylation agent.

24. The process of claim 1 wherein the frequency with which the zone A reactors and the zone B reactors cycle back and forth between the alkylation mode and the mild regeneration mode ranges from once per 10 hours to 10 times per hour.

25. The process of claim 1 wherein the one or more additional solid acid alkylation catalyst-containing reactors replace one or more of the reactors in zone A or zone B to allow the catalyst in the replaced reactor or reactors to be subjected to high-temperature regeneration at a temperature of at least 423 K.

26. The process of claim 25 wherein the high-temperature regeneration is performed at a temperature in the range of 423–873 K.

27. The process of claim 1 wherein at least one reactor contains at least two catalyst beds.

28. The process of claim 27 wherein the most downstream catalyst bed in the at least one reactor containing at least two catalyst beds is larger than the other catalyst beds in the same reactor.

29. The process of claim 27 wherein the most downstream catalyst bed in the at least one reactor containing at least two catalyst beds contains a different catalyst than the other catalyst beds in the same reactor.

30. The process of claim 27 wherein alkylation agent is introduced into the at least one reactor via at least two injection points.

31. The process of claim 30 wherein one injection point is positioned below the most upstream catalyst bed in the reactor and the other injection points are positioned below each of the subsequent catalyst beds.

32. The process of claim 1 wherein the alkylatable compound is isobutane and the alkylation agent comprises $C_3$–$C_5$ alkenes.

33. The process of claim 32 wherein the alkylation agent is butene or a mixture of butenes.

34. The process of claim 1 wherein the process is conducted at a pressure in the range of 5–40 bar.

35. The process of claim 1 wherein the temperature in the alkylation mode zone is in the range of 293–423 K.

36. The process of claim 35 wherein the temperature, expressed in K, in the mild regeneration mode zone does not differ from the temperature in the alkylation mode zone by more than 20%.

37. The process of claim 36 wherein the temperature in the mild regeneration mode zone is substantially the same as the temperature in the alkylation mode zone.

* * * * *